(12) United States Patent
Evans et al.

(10) Patent No.: US 6,322,499 B1
(45) Date of Patent: Nov. 27, 2001

(54) PIVOTAL AND ILLUMINATED SAPHENOUS VEIN RETRACTOR

(75) Inventors: Douglas Gerald Evans, Chamblee; Donna DiMarco Holland, Atlanta, both of GA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 09/490,130

(22) Filed: Jan. 20, 2000

(51) Int. Cl.$^7$ ......................................................... A61B 1/32
(52) U.S. Cl. ........................... 600/212; 600/215; 600/210; 600/235; 600/245; 600/213
(58) Field of Search ...................... 600/185, 191, 600/193, 196, 190, 201, 210, 212, 215, 226, 235, 245, 213; 606/190

(56) References Cited

U.S. PATENT DOCUMENTS

| | | |
|---|---|---|
| 2,646,037 * | 7/1953 | Cook et al. . |
| 3,638,644 * | 2/1972 | Reick . |
| 4,052,980 | 10/1977 | Grams et al. . |
| 4,597,030 | 6/1986 | Brody et al. . |
| 4,765,701 | 8/1988 | Cheslak . |
| 4,836,190 | 6/1989 | Zwick . |
| 4,934,352 * | 6/1990 | Sullivan, Jr. . |
| 4,996,976 | 3/1991 | Nakagawa . |
| 5,005,108 | 4/1991 | Pristash et al. . |
| 5,035,232 | 7/1991 | Lutze et al. . |
| 5,514,076 | 5/1996 | Ley . |
| 5,514,077 | 5/1996 | Rabban . |
| 5,667,480 | 9/1997 | Knight et al. . |
| 5,722,934 | 3/1998 | Knight et al. . |
| 5,725,479 | 3/1998 | Knight et al. . |
| 5,730,748 | 3/1998 | Fogarty et al. . |
| 5,776,159 | 7/1998 | Young . |
| 5,797,947 | 8/1998 | Mollenauer . |
| 5,853,417 | 12/1998 | Fogarty et al. . |
| 5,904,650 | 5/1999 | Wells . |
| 5,921,919 * | 7/1999 | Chin et al. ............................ 600/217 |
| 5,967,971 | 10/1999 | Bolser . |
| 5,972,010 | 10/1999 | Taheri . |
| 6,007,487 * | 12/1999 | Foley et al. ....................... 600/210 X |
| 6,033,361 * | 3/2000 | Co et al. .............................. 600/210 |
| 6,042,538 * | 3/2000 | Puskas ............................. 600/210 X |
| 6,196,968 * | 3/2001 | Rydin et al. .......................... 600/210 |

FOREIGN PATENT DOCUMENTS

| | | | |
|---|---|---|---|
| 2133694 * | 8/1984 | (GB) | .................................... 600/245 |
| WO 97/13465 | 4/1997 | (WO) . | |
| WO 99/01696 | 1/1999 | (WO) . | |
| WO 99/56633 | 11/1999 | (WO) . | |

OTHER PUBLICATIONS

Auto Suture Company, The Mini–Harvest System (1996).

(List continued on next page.)

*Primary Examiner*—Jeffrey A. Smith
(74) *Attorney, Agent, or Firm*—Richard D. Allison; Thomas J. DesRosier

(57) ABSTRACT

An illuminated surgical retractor for illuminating a subcutaneous surgical field in the space between a vessel, such as the saphenous vein, and the subcutaneous tissue when the illuminated retractor is used to retract the subcutaneous tissue away from the superior surface of the vessel, the illuminated surgical retractor having a handle member pivotally connected at an acute angle to a first elongate section and a second elongate section that is releasably connected to the first elongate section and a portion of the second elongate section defining an illumination input end portion which is optically coupled to a light source so that the second elongate section is substantially illuminated, and, a shroud member is positioned on the proximal end portion of the first elongate section to aid in the dissection of the intervening tissue.

36 Claims, 11 Drawing Sheets

OTHER PUBLICATIONS

Design News, Bypass Surgery Made Easier, Disposable Instruments, Made from Standard Plastics, Key to Minimally Invasive Procedure for Extracting Veins, Gary Chamberlain, Senior Editor, pp. 57–58, 60, 62 (Jan. 6, 1997).

Dimitri, W. R. et al., A Quick and Atraumatic Method of Autologous Vein Harvesting Using the Subcutaneous Extraluminal Dissector, J. Cardiovasc. Surg., vol. 28, pp. 103–111 (1987).

Dregelid, E. et al., Endothelial Cell Injury in Human Saphenous Veins After Manipulation and Tweezer Grasping, J. Cardiovasc. Surg., vol. 29, pp. 464–469 (1988).

Gundry, Steven R. et al., Optimal Preparation Techniques for Human Saphenous Vein Grafts, Surgery, No. 6, pp. 785–794 (Dec. 1980).

Hauer, G. et al., Endoscopic Subfascial Discission of Perforating Veins, Surg. Endosc., vol. 2, pp. 5–12 (1988).

Meldrum–Hanna, W. et al., Long Saphenous Vein Harvesting, Aust. N.Z. J. Surg., vol. 56, pp. 923–924 (1986).

Moazami, Nader et al., Minimally Invasive Greater Saphenous Vein Harvesting for Coronary Artery Bypass Surgery, Surgical Rounds, pp. 94–97 (Mar. 1997).

Rashid, A. et al., Subcutaneous Technique for Saphenous Vein Harvest, The Annals of Thoracic Surgery, vol. 37, No. 2, pp. 169–170 (Feb. 1984).

Snowden Pencer DSP, The Diamond–Line of Surgical Instruments Brochure, Tebbetts EndoPlastic Instrument System, 1995.

Snowden Pencer DSP, EndoCABG System, Innovative Instrumentation for Endoscopic Coronary Artery Bypass Grafting, 1996.

Surgical Physician Assistant, Minamally Invasive Vein Harvesting, John Lee, pp. 26–32, Nov./Dec. 1996.

Wheatley, D.J., Autocoronary Bypass Grafting Techniques, Surgery of Coronary Artery Disease, pp. 348–349 (Date Unknown).

* cited by examiner

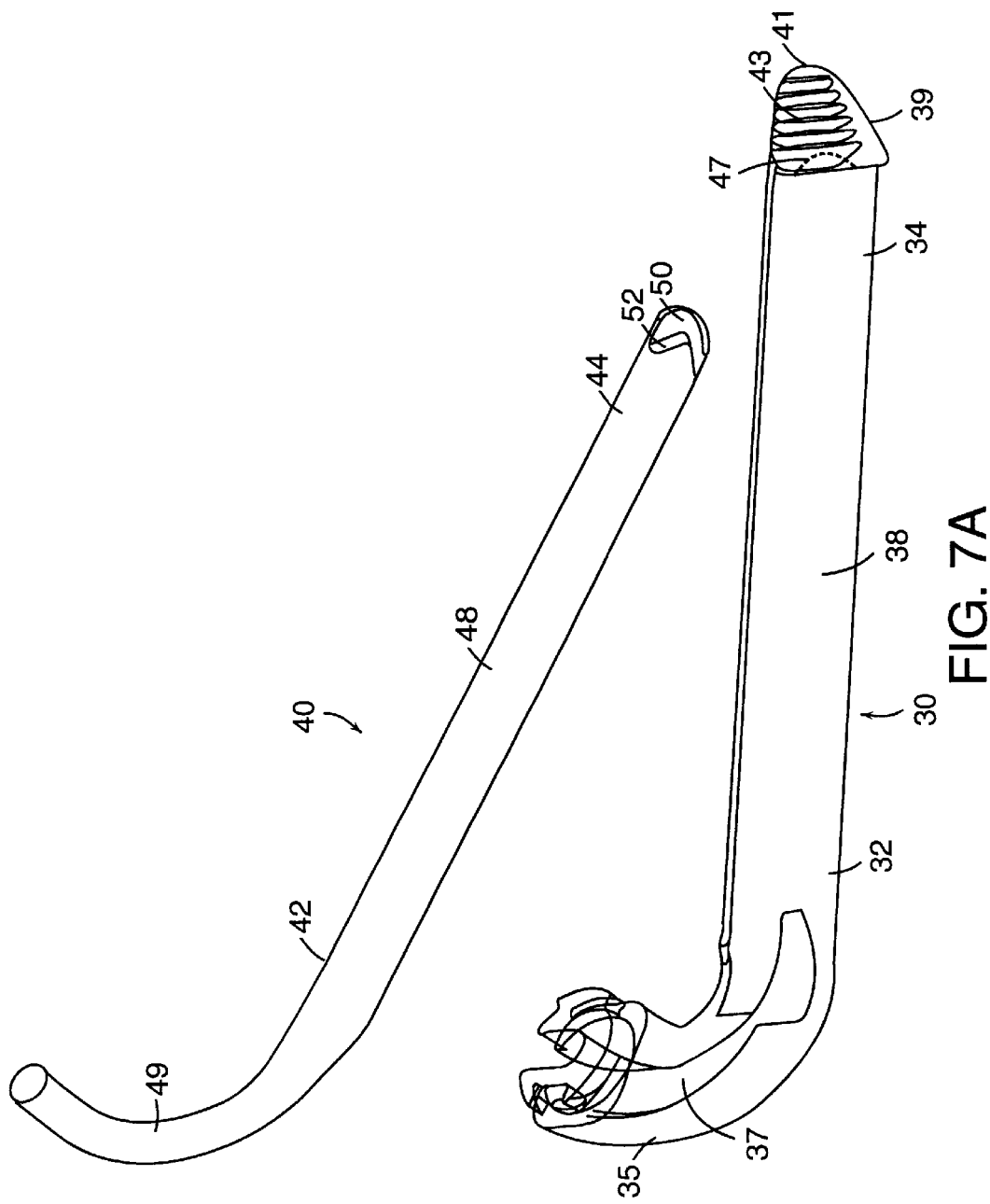

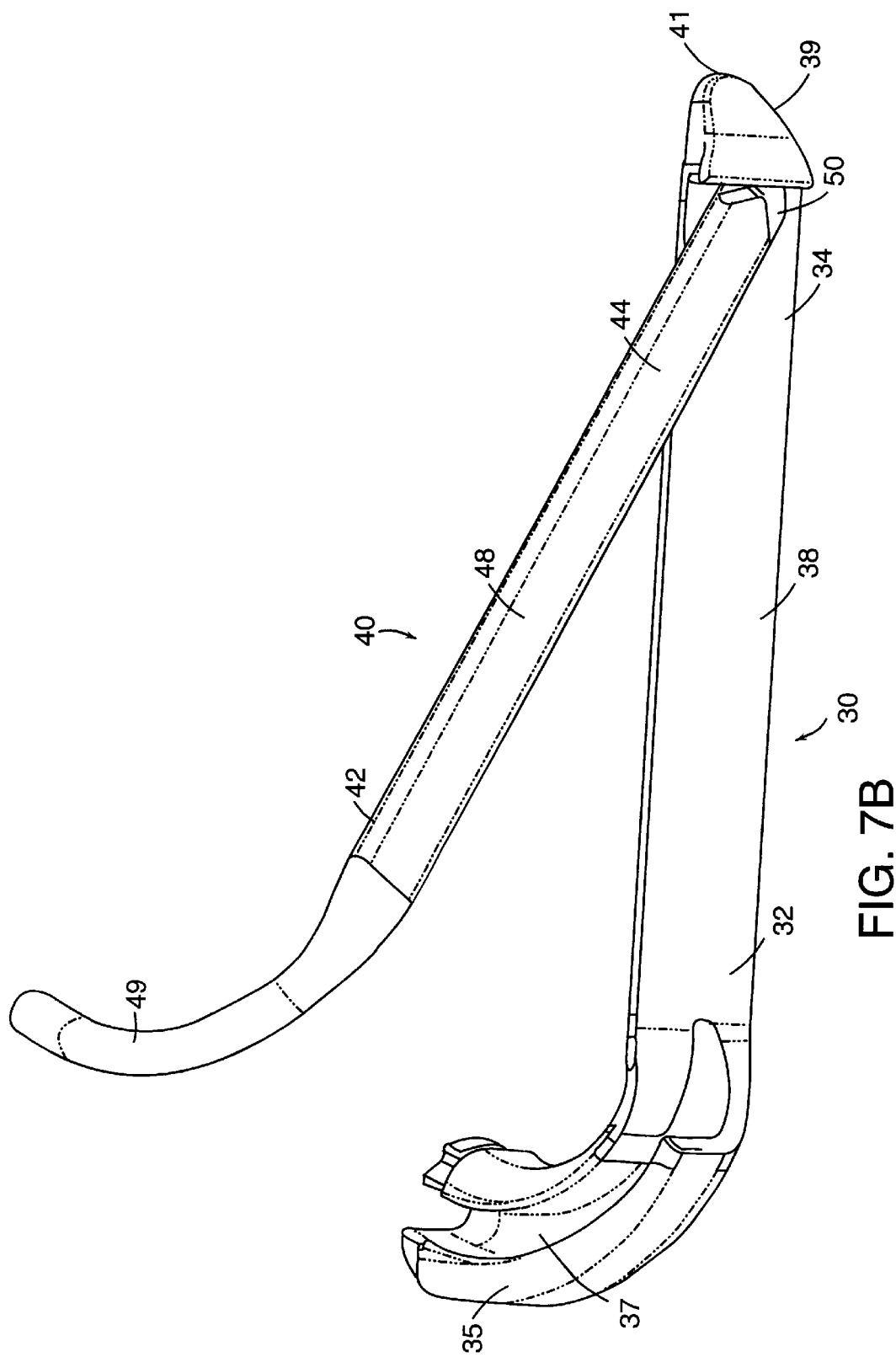

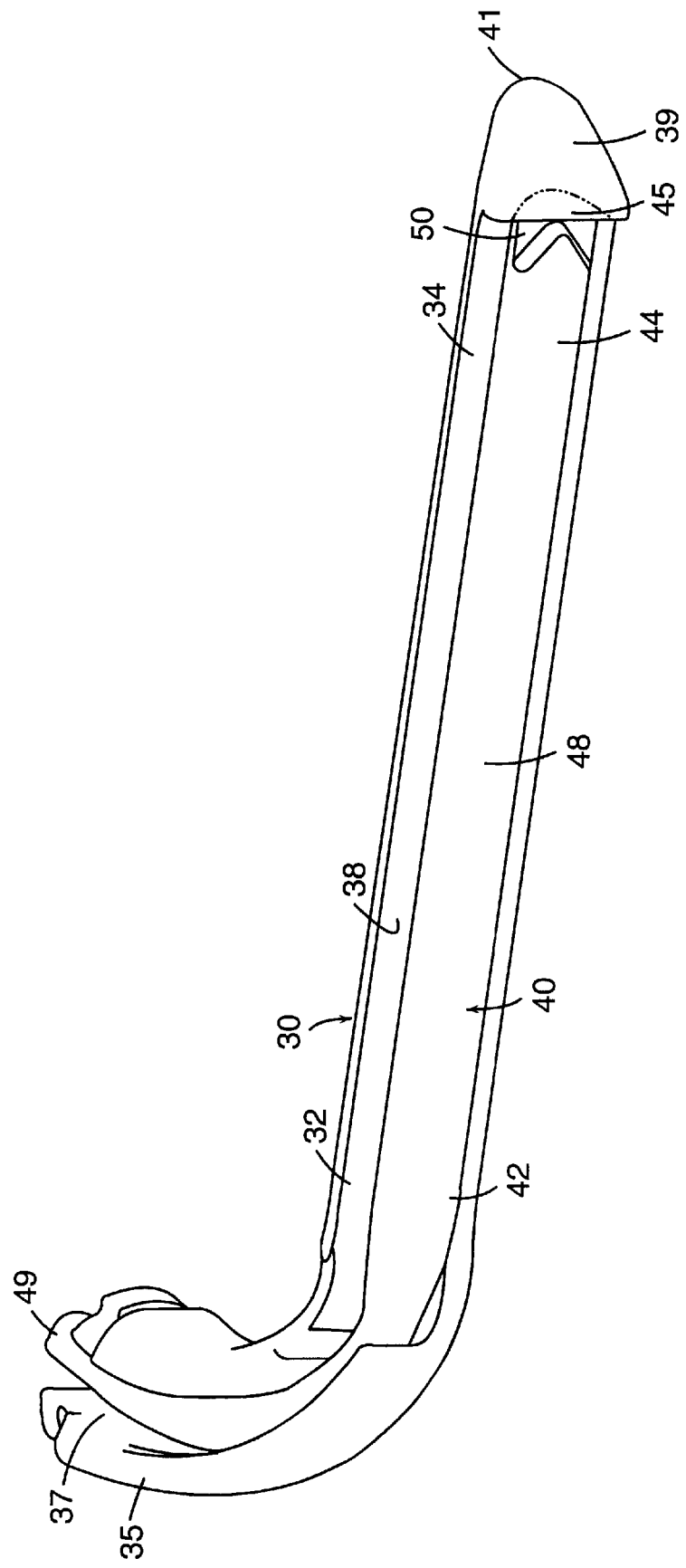

PIVOTAL AND ILLUMINATED SAPHENOUS
VEIN RETRACTOR

BACKGROUND OF THE INVENTION

1. Field of the Invention

The present invention relates, in general, to vessel harvesting and, in particular, to a new and useful illuminated retractor for creating a working space for dissecting instruments in support of a surgical procedure such as a coronary bypass procedure or other types of procedures which require the harvesting of a vessel or tissue.

The present application is co-pending with U.S. Ser. No. 09/071,786 filed on May 1, 1998 (pending) and boffi applications are commonly assigned to the assignee of the present application.

2. Background of the Invention

In certain surgical procedures, it is necessary to remove a section of a blood vessel from a patient for use in another part of the patient's body or for transplanting into a second patient's body. For example, a section of the saphenous vein or radial artery may be removed for use in coronary bypass surgery to replace coronary arteries which supply blood to the heart. As a result of aging and disease, coronary arteries may become blocked by plaque deposits, stenosis, or cholesterol. In some instances, these blockages can be treated with angioplasty, atherectomy or stent placement, and coronary bypass surgery is not required. Coronary bypass surgery is required when these other methods of treatment cannot be used or have failed to clear the blocked artery.

In the coronary bypass surgery, a blood vessel is harvested from elsewhere in the body and grafted into place between the aorta and the coronary artery beyond the point of blockage. It is preferred to use a vessel taken from the patient undergoing the bypass surgery since the patient is a ready source of suitable veins or arteries that will not be rejected by the body after transplantation. The saphenous vein in the leg is the most commonly used substitute for small arteries such as the coronary arteries because the saphenous vein is typically 3 to 5 mm in diameter (about the same size as the coronary arteries) and it is thus the preferred vein for use in coronary bypass surgery. Also, the venous system of the legs is sufficiently redundant so that after removal of the saphenous vein, other veins that remain in the leg are adequate to provide return blood flow. The cephalic vein in the arm is an alternative that is sometimes used. Furthermore, the radial artery is increasingly being used as a replacement in order to provide a readily accessible artery for use in the coronary bypass surgery.

The conventional, non-endoscopic, surgical procedure for the removal of the long saphenous vein as a graft in coronary and vascular surgery may require the physician's assistant to make one long incision from the groin to the knee or ankle of the patient's leg to allow access to the saphenous vein. Alternatively, if the physician's assistant uses several long incisions, one or more small skin bridges are formed along the line of the incisions. While handling of the vein should be kept to a minimum, the vein must be separated from the connective tissue, and that requires the application of some force. After exposing the vein, the physician's assistant grasps it with their fingers while stripping off the surrounding tissues with dissecting scissors or other scraping instruments. The physician's assistant uses their fingers and/or blunt dissection tools to separate the vein from the surrounding tissue. To reach under the small skin bridges, the physician's assistant lifts the skin with retractors and dissects the vein free. When the vein has been completely separated from the surrounding tissue and the tributary veins that feed into the saphenous vein, the physician's assistant cuts the proximal and distal end portions of the vein and removes the vein from the leg. After removal, the vein is prepared for implantation into the graft site and the incisions made in the leg are closed, for example by suturing or staples.

A major disadvantage of the conventional, non-endoscopic, vessel harvesting operation, the vessel harvesting operation is that it is very traumatic in its own right. In the case of coronary artery bypass surgery, the saphenous vein retrieval operation is carried out by a surgical nurse or physician's assistant immediately before the chest of the patient is opened by the surgeon. Therefore, it is important that this part of the operation also be performed in a timely manner so as not to tie up the surgical suite and delay the surgeon. Unfortunately, the vein harvesting operation is often the most troublesome part of the operation for the patient. The long incision, or incisions, involves the risk of injury to the medial lymph bundle, various nerves and the risk of infection of the extensive operation site itself. The leg may thus, in addition to being very painful, be slow to heal, or may not heal properly, particularly in those patients who have poor circulation in their extremities, and can consequently hinder the patient's recovery from the operation. It is therefore desirable to perform the vessel harvesting procedure in as minimally or less invasive a manner as feasible.

One alternative for minimally invasive vessel harvesting uses an endoscopically controlled vessel removal system. In contrast to the open long incision method, the physician's assistant can limit the procedure to 2 or 3 small uincisions on the proximal thigh, at the level of the knee joint and perhaps the inner malleolus. Such minimally invasive or endoscopic vessel harvesting is known in the surgical field. Viewing the tools through an endoscope or laparoscope, or a video display from the endoscope, the physician's assistant typically grasps and holds the saphenous vein with a grasper that is introduced through the lumen of an endoscope. After connective tissue is dissected from around the vein, the vein is ligated and transected and then removed via the lumen of the endoscope. Alternatively, as the vein is withdrawn into the lumen of the endoscope, the endoscope may be maneuvered along the length of the vein while side branches of the vein are ligated and transected whenever encountered. The endoscopic removal methods leave the surrounding tissues intact and the vein is prepared and removed under visual conditions.

There are several drawbacks to the endoscopic vessel harvesting method described above. First, the endoscopic or laparoscopic methods require the physician's assistant or surgical nurse to view the tools and the operating field through the distorted visual perspective provided by the endoscope, laparoscope, or the video display from the endoscope. This is a poor substitute for the actual visualization of the surgical field by the naked eye. Second, compounding the first drawback, in practicing this method there is limited visibility of the saphenous vein and its side branches because viewing is limited to the area immediately in front of the endoscope. Third, the illumination within the subcutaneous space created by this type of endoscope is also limited to the light emitted directly at the distal portion of the endoscope. Another drawback to this type of procedure is that the side branches of the saphenous vein limit the maneuverability of the endoscope since the outer edge of the endoscope body is prevented from advancing along the trunk of the saphenous vein until the encountered side branches are ligated and transected. Once freed, the endoscope is then maneuvered until the next side branch is encountered. Moreover, it has been found that methods that utilize this type of endoscope, i.e. an endoscope having a lumen, provide a working space that is very restricted because the side walls of the scope body constrain the working instrumentation to a limited area. Because of this, there is a significant learning curve in order to safely and efficiently practice this procedure. It is therefore desirable to use a procedure that overcomes the drawbacks inherent to the endoscopic vessel harvesting method.

In an alternative less invasive technique for harvesting a blood vessel that overcomes the drawbacks of the endoscopic method, the physician's assistant utilizes 2–3 small incisions on the proximal thigh, at the level of the knee joint and perhaps the inner malleolus. This approach creates several long skin bridges by lifting the tissue between the incisions. To reach under the skin bridges, the physician's assistant lifts the skin with retractors and exposes the vein. After exposing the vein, the physician's assistant will use their fingers and/or blunt dissection tools to separate the vein from the surrounding tissues. It is desirable for the retractor to have some means of aiding the dissection of the surrounding tissues so that the trauma and time required for the procedure is limited. When the vein has been completely separated from the surrounding tissue and the tributary veins that feed into the saphenous vein, the physician's assistant cuts the proximal and distal end portions of the vein and removes the vein from the leg. After removal, the vein is prepared for implantation into the graft site, and the 2–3 small incisions made in the leg are sutured or stapled closed. Because the dissection of the vein is accomplished by the physician's assistant's fingers and/or by blunt dissection, this technique may be accomplished in a more timely manner than the endoscopic method. This alternative technique is a less invasive technique that, just like the endoscopic method described above, consequently minimizes the risks and complications of the surgery.

This technique overcomes the endoscopic method drawbacks of limited movement and limited workspace of the dissection and ligation instrumentation and the limited and distorted visual perspective provided by the endoscope, laparoscope, or the video display from the endoscope. However, one drawback remains. Using prior art retractors, the illumination of the surgical field is poor. By necessity of the less invasive nature of the procedure, the vessel harvesting procedure is primarily conducted under the long skin bridges left between the small incisions. Because the skin bridges are so long, it is difficult to sufficiently illuminate the subcutaneous space between the vessel and the subcutaneous tissue when retractors known in the art are used to retract the tissue way from the superior surface of the vessel. With insufficient illumination of the surgical field, the advantages of the physician's assistant being able to maneuver freely and to optically visualize the surgical field using the benefit of their own vision during the course of the minimally invasive procedure are eroded. It is therefore desirable to provide a means of providing illumination to the subcutaneous space formed by the retractor so that the physician's assistant can efficiently view and operate in the entire surgical field exposed by the retractor.

SUMMARY OF THE INVENTION

The present invention overcomes the disadvantages of the prior art. As shown in the drawings, the present invention provides an illuminated retractor for illuminating the subcutaneous space between a vessel, such as the saphenous vein which is located in a patient's leg, and the subcutaneous tissue when the illuminated retractor is used to form a skin bridge by retracting the tissue away from the blood vessel.

In the contemplated less invasive operation for harvesting a blood vessel, the physician's assistant utilizes 2–3 small incisions on the proximal thigh, at the level of the knee joint and perhaps the inner malleolus. This procedure results in several long skin bridges between the incisions. To expose the length of the vein remaining under the skin bridges, the physician's assistant lifts the skin and the subcutaneous tissue with the illuminated retractor. Once the retractor is positioned, the physician's assistant may use an existing external retention device to support the retractor and maintain the skin bridge while the physician's assistant dissects the tissue from around the blood vessel. The external retention device preferably attaches to the side of the table and is adjustable to attach to a connector on the retractor and retain the retractor in the desired position.

The illuminated retractor provides a large, well illuminated surgical field, which preferably extends the substantial length of the retractor within the subcutaneous space created by the retractor. With the vein thus exposed, the physician's assistant uses their fingers and/or blunt dissection tools to separate the vein from the surrounding tissues. When the vein has been completely separated from the surrounding tissue and the tributary veins that feed into the saphenous vein, the physician's assistant cuts the proximal and distal end portions of the vein and removes the vein from the leg. After vein removal, the 2–3 small incisions made in the leg are sutured or stapled closed and the vein harvesting procedure is completed.

The illuminated surgical retractor preferably has a handle member, a first elongate section and a second elongate section. The handle member is preferably contoured to be gripped by the operating physician's assistant and is pivotally connected to the first elongate section at the distal end portion of the first elongate section, thus permitting one-handed use by the physician's assistant. The handle member permits the retractor to be lifted at any desired angle with respect to the axis of the blood vessel. Thereafter a pulling force may be applied to the handle member so that a corresponding pulling or retraction force is applied to the subcutaneous tissue via the first elongate section. This force creates the subcutaneous space beneath the subcutaneous tissue when the subcutaneous tissue is drawn away from the tissue surrounding the blood vessel. The handle member may also have an elongated rod extend portioning from the opposite end portion of the handle member that allows the retractor to be maneuvered into the desired position by the physician's assistant and then fixed in the desired relative position by clamping or grasping the retractor with the available operating table retention mechanisms.

The first elongate section preferably has a first elongate proximal end portion, a first elongate distal end portion, a first elongate outer surface, and a first elongate inner surface. The first elongate section preferably functions to transfer to lifting and/or insertion forces from the handle member to the skin bridge of the patient. Similarly, the second elongate section, which may be substantially transparent, has a second elongate proximal end portion, a second elongate distal end portion, a second elongate outer surface and a second elongate inner surface. The second elongate section preferably functions to perform the illumination feature of the present invention. The second elongate outer surface of the second elongate section is preferably slidable laterally with respect to a portion of the first elongate section and into engagement with the first elongate section such that the first and second elongate sections are substantially adjacent to each other and are generally aligned with each other. As used herein, reference to the proximal end portion of an element is the end portion of an element that is spaced apart from the handle member and reference to the distal end portion of an element is the end portion of an element that is generally adjacent to or closer to the handle member of the preferred form of the present invention The first elongate proximal end portion preferably has a rounded shape or a smoothly radiused pointed shape that allows the retractor to be pushed into the small incision made by the physician's assistant and thrust forward and maneuvered through the connective tissue between the subcutaneous tissue and the vessel to be harvested. Additionally, the first elongate proximal end portion preferably includes a nose cone or shroud member thereon to assist in the tissue dissection and to receive and retain the proximal end portion of the second elongate section therein. In the preferred form of the shroud member, the proximal end portion of the second elongate section is insertable laterally into the shroud member on the proximal end portion of the first elongate section. The shroud member preferably extends upwardly a small distance above the proximal end portion of the first elongate section and also slightly below the proximal end portion of the first elongate section. The upper and proximal surface of the shroud member is preferably tapered and oriented at an angle of about forty-five degrees with respect to the first elongate section to provide a low profile extension that assists in the dissection of the tissue while the lower and distally extending portion protects and retains the proximal end portion of the second elongate section therein.

The proximal end portion of the second elongate section preferably has a rounded shape or, alternatively, a smoothly radiused pointed shape. The shape of the second elongate section proximal end portion is preferably complementary to the shape of the recess in the shroud member of the first elongate section proximal end portion so that the proximal end portion of the retractor, when the first and second elongate sections are connected, can readily penetrate the connective tissue under the subcutaneous tissue as the retractor is inserted into the small incision and maneuvered into position and so that the proximal end portion of the second elongate section is securely retained in the shroud member. Additionally, the proximal end portion of the second elongate section is also preferably configured to direct light forwardly of the retractor during use.

The top surface of the shroud member of the illuminated surgical retractor may also form a bent dissecting tip which extends from the first elongate section at the proximal end portion of the first elongate section. This bent dissecting tip allows the physician's assistant to use the shroud member as a dissecting device as the retractor is inserted and maneuvered around and/or through the connective tissue surrounding the vessel to be harvested. As described below, this bent dissecting tip may also include serrations thereon to assist in the dissection of the tissue and to assist in retaining the retractor in the desired position during this procedure.

In order to enhance the reflective qualities of the illuminated retractor, the first elongate inner surface of the first elongate section may preferably include a mirrored surface thereon. Also, the second elongate inner surface of the second elongate section may preferably have a machined micro-lens surface thereon that refracts the light forwardly at a desired angle. Alternately, the second elongate section may have a graded dot screen surface. The mirrored surface of the first elongate inner surface and the machined surface of the second elongate inner surface function to minimize the light intensity loss of the light energy that is provided to the surgical field by the illuminated retractor. Alternately, the second elongate inner surface may be reflective to direct to the illumination outwardly from the second elongate outer surface. Furthermore, the second elongate section may be constructed so as to reflect to the illumination forwardly from the second elongate section to illuminate the skin bridge forwardly of the illuminated surgical retractor. For example, the second elongate section may be formed so that the light is transmitted at a forward angle that is between about 15 and 75 degrees and more preferably between about 30 and 60 degrees relative to the second is elongate section while also scattering the illumination to the sides of the retractor as desired.

The preferred form of the retractor also includes a connector between the handle member and the first and second elongate sections. This connector is preferably a twist type of connection between the first elongate section and the handle member. This connection is preferably simple to make, such as by a onequarter turn, and is secure to ensure that the first and second elongate sections remain attached to the handle member as the skin bridge is created and maintained by the physician's assistant. The connector also connects the handle member to the second elongate section to ensure that the light energy travels from the light source; through the handle member and into the second elongate section. The light energy fills the second elongate section and turns the second elongate section into a "light pipe." The light energy is, in turn, radiated from the second elongate section into the subcutaneous space between the vessel and the subcutaneous tissue exposed by the retractor. In this manner, light can be provided from the light source via the optical cable to the illumination input end portion of the second elongate section so that the second elongate section is illuminated, which results in an illuminated surgical field.

A further feature of the preferred form of the present invention is that the proximal end portion or heal portion of the illuminated retractor is formed to shield the user from the light created by the distal end portion of the second elongate section. Additionally, the first elongate section may include a side channel in a shaft portion thereof to allow a shaft shaped portion second elongate section to be inserted therethrough to allow the second elongate section to be replaceably mounted onto the first elongate section as desired. A further feature of the heal portion of the illuminated retractor of the present invention is that at least a portion of the shaft shaped portion and/or the distal end portion of the second elongate section is preferably spaced apart from at least a portion of the shaft portion and/or the distal end portion of the first elongate section to ensure that there is no heat buildup between these elements of the illuminated surgical retractor.

Yet another feature of the preferred form of the present invention is that the light cable passes through the handle member of the retractor and a portion of the handle member may be formed to allow the light generated by the light cable to be observed through the body of the handle member to enable the user to readily determine whether or not the light source for the retractor is in operation. Additionally, a further preferred embodiment may include a second connection that may be used to connect a standard light cable at the top of the handle member to a shortened light cable in the handle member of the retractor so that the handle member and elongate members may be packaged and/or sterilized separately. Alternately, the light cable may be allowed to pass through the handle member for direct connection to the light source and the second elongate member as desired.

BRIEF DESCRIPTION OF THE FIGURES OF THE DRAWINGS

Embodiments of the invention are described by way of example with reference to the accompanying drawings, in which:

FIGS. 7A, 7B and 7C are perspective views of the preferred form of the first elongate section and the second elongate section of the present invention showing the relationship between the first elongate section and the second elongate section.

DETAILED DESCRIPTION OF THE INVENTION

Figure 1:
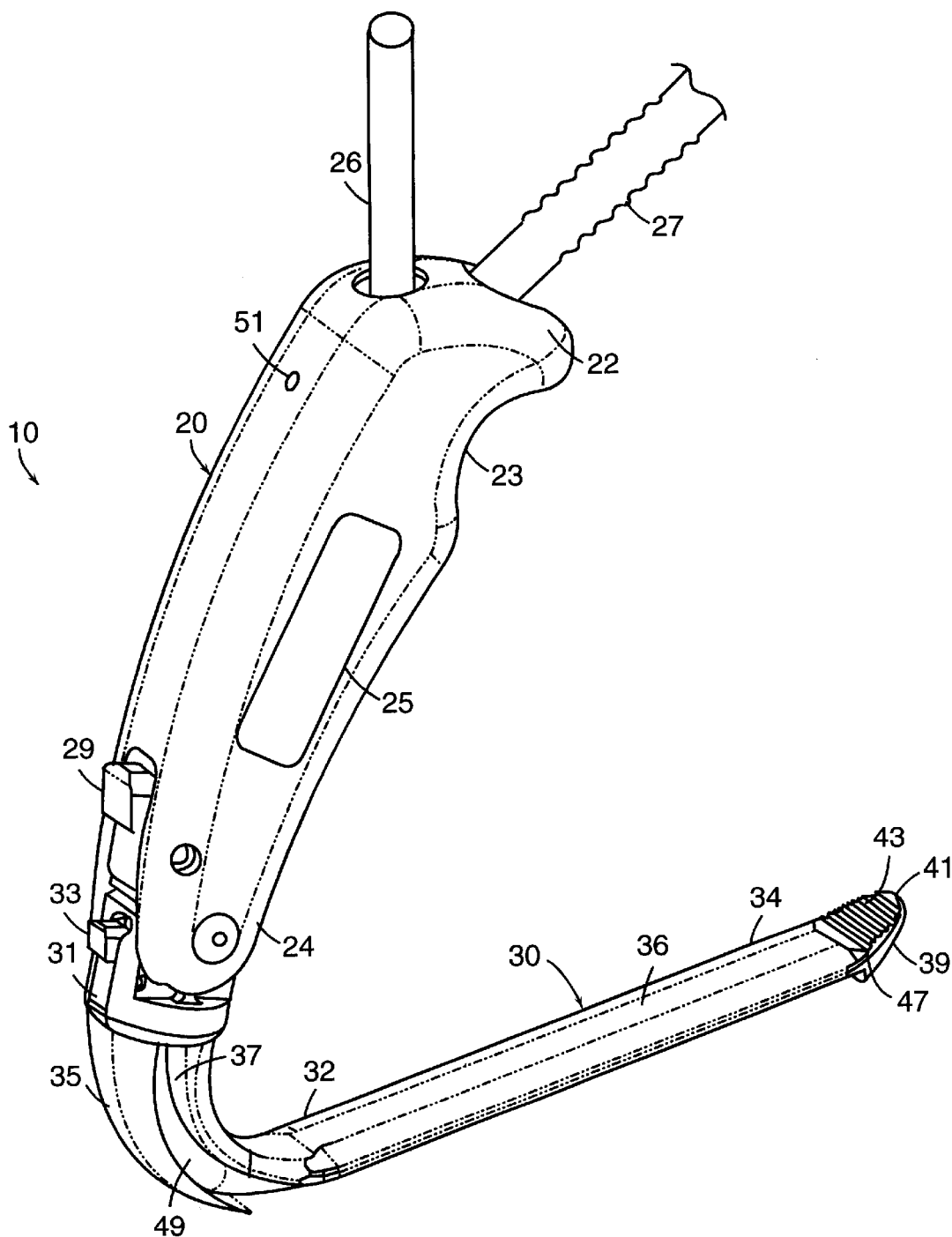
FIG. 1 is a perspective view of the preferred form of an illuminated retractor according to the present invention.
Figure 2:
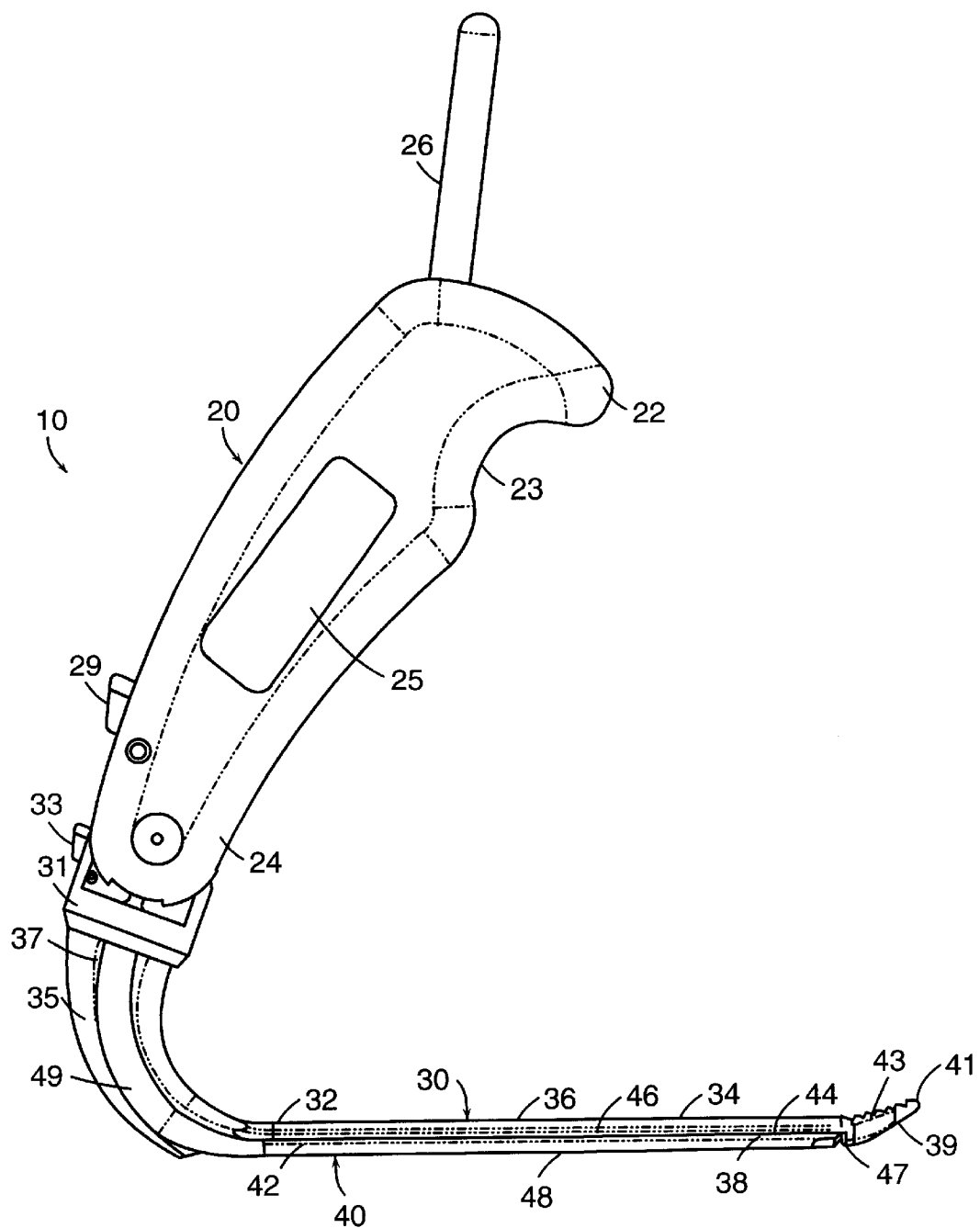
FIG. 2 is an enlarged side view of the preferred form of an illuminated retractor according to the present invention with the optical cable removed for clarity.
Figure 3:
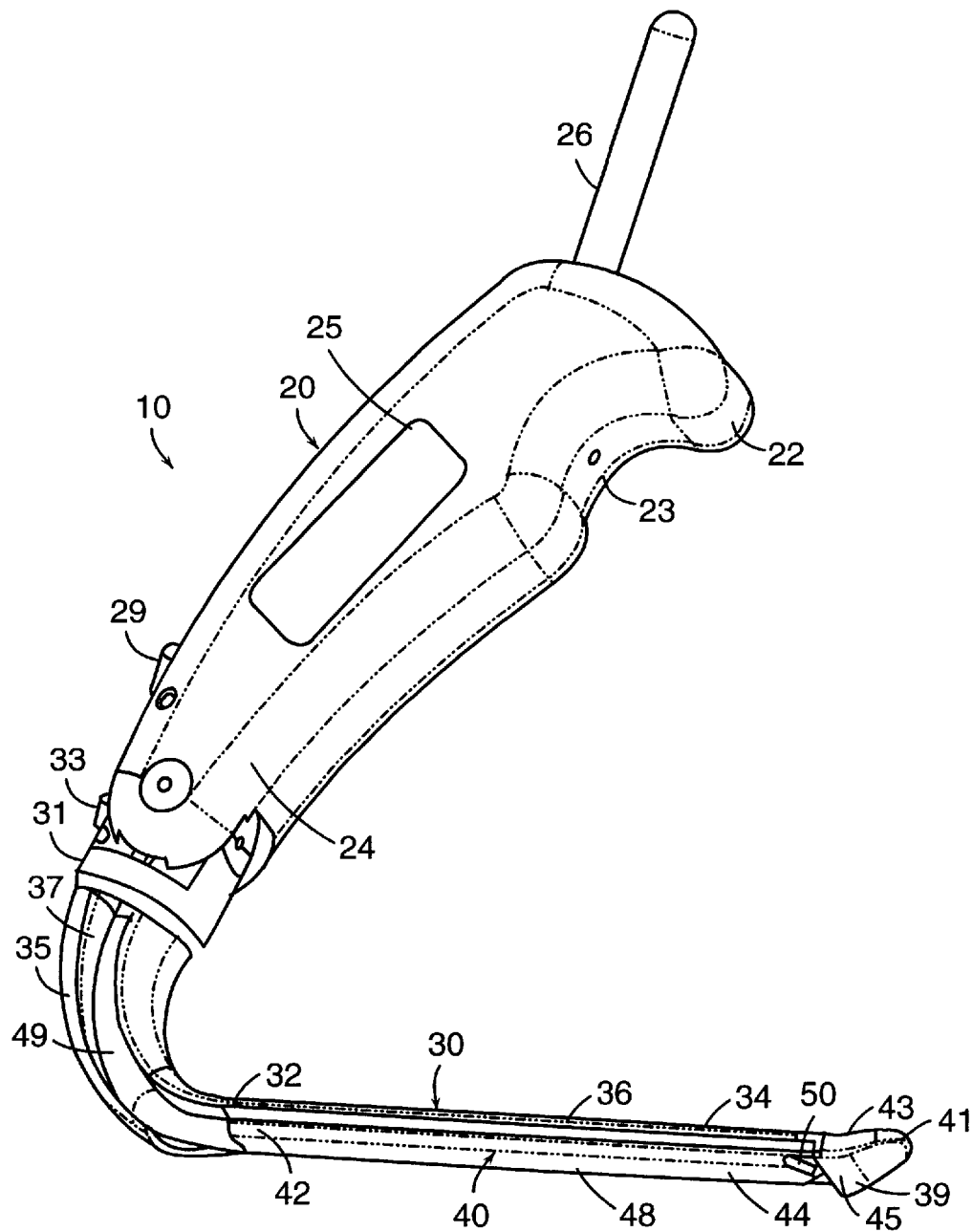
FIG. 3 is a perspective view of the preferred form of an illuminated retractor according to the present invention with the optical cable removed for clarity.
Figure 4:
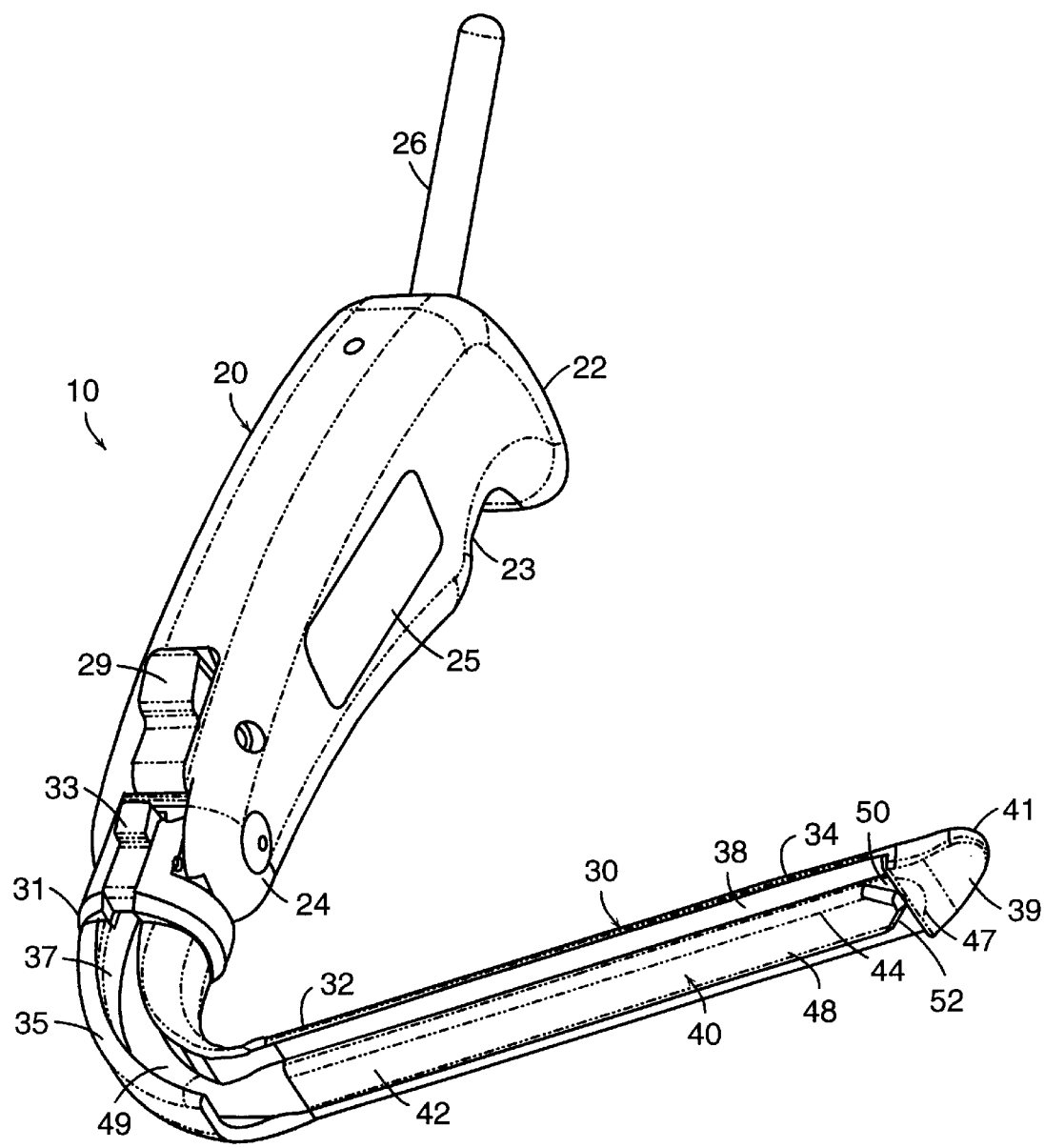
FIG. 4 is a perspective view of the preferred form of a semi-assembled illuminated retractor according to the present invention with the handle member oriented at a 90 degree angle to the first elongate section and with optical cable removed for clarity.
Figure 5:
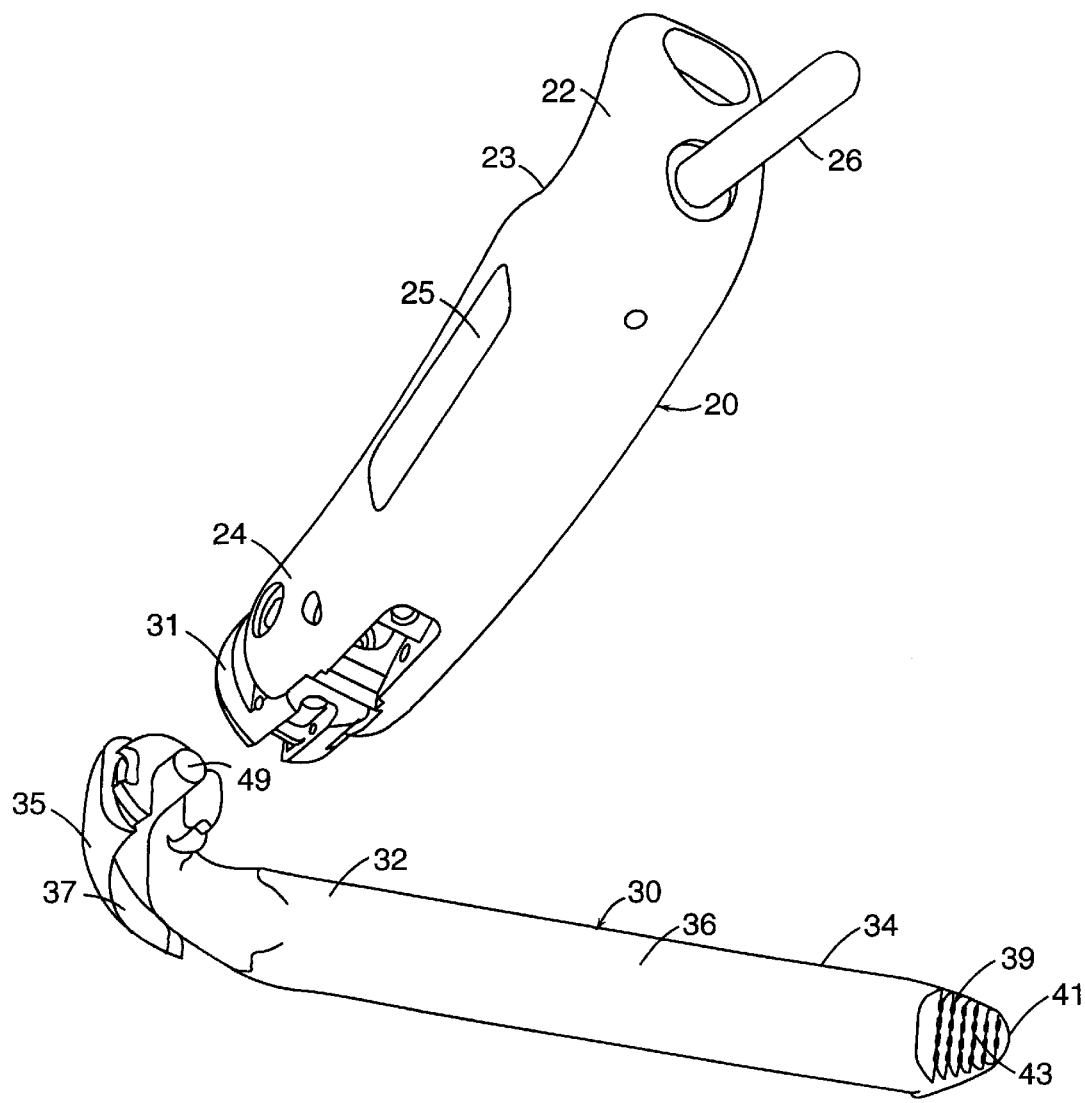
FIG. 5 is a further exploded perspective view of the illuminated retractor according to the present invention showing the handle member separated from the first elongate section and the second elongate section with the optical cable removed for clarity.
Figure 6:
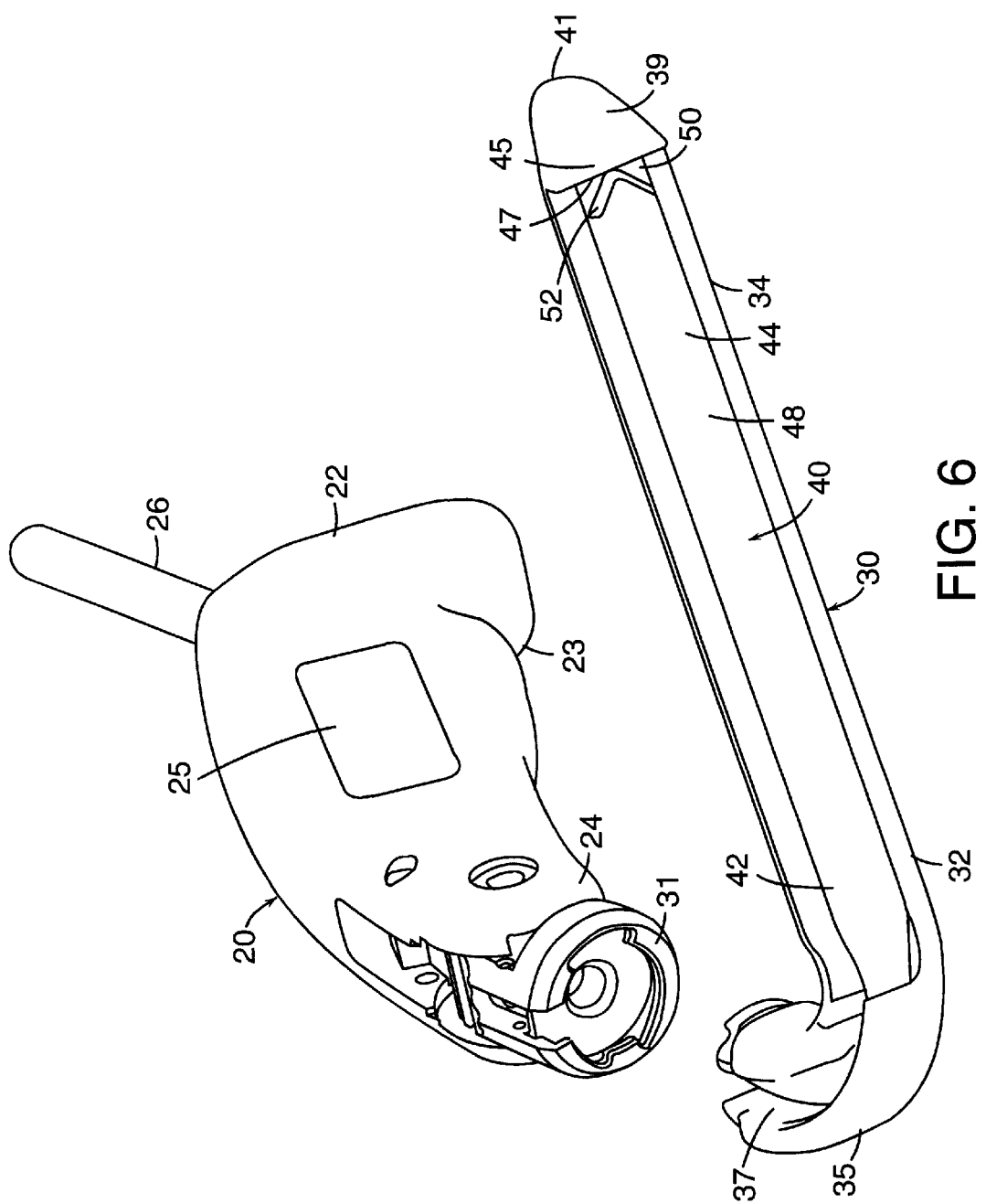
FIG. 6 is a perspective view of the preferred form of an illuminated retractor according to the present invention showing the bottom surfaces of the first elongate section and the second elongate section with the optical cable removed for clarity.

The present invention provides an illuminated retractor for illuminating the subcutaneous space between a blood vessel or other, such as the saphenous vein or the radial artery, and the subcutaneous tissue when the illuminated retractor is used to retract the tissue away from the superior surface of the vessel or desired tissue.

As shown in the drawings, the present invention relates to an illuminated surgical retractor 10 having a handle member 20, a first elongate section 30, a second elongate section 40, and a twist connector 31.

The handle member 20 is an elongate and generally cylindrical member that has a first top handle member end portion 22 and a second bottom handle member end portion 24. The second handle member end portion 24 of the handle member 20 is connected to the first elongate section 30 at the shaft portion 35 distally of the distal end portion 32 on the first elongate section 30 via a twist connector 31 for permitting one-handed setup and use by the physician's assistant. The best combination of retractor mobility and application of retractive or pulling force occurs when the acute angle α between the handle member 20 and the first elongate section 30 is between about 30 and 90 degrees and more preferably between about 45 and 75 degrees. The handle member 20 permits the retractor 10 to be lifted at nearly any angle with respect to the axis of the blood vessel. Therefore, when an upward or pulling force is applied to the handle member 20, a retractive force is applied to the subcutaneous tissue via the first elongate section 30 to create a subcutaneous space or skin bridge beneath the subcutaneous tissue when the subcutaneous tissue is drawn upwardly by the first elongate outer surface 36 of the first elongate section. Application of this force causes the separation of the tissue around a portion of the blood vessel to form a skin bridge that allows the user to dissect tissue from around the target blood vessel.

The handle member 20 of the retractor 10 also preferably includes a finger grip surface 23 that is preferably contoured to be gripped by the hand of a physician's assistant to provide more tactile feel and feedback as well as increasing the physician's assistant's comfort in using and maneuvering the retractor. The handle member also preferably includes a window area 25 to provide visual confirmation that the light source is operative and the retractor 10 is properly setup. Therefore, when the retractor 10 is illuminated, the window area 25 is illuminated so that the physician's assistant and any other people in the surgical suite will be able to readily determine that the retractor is in use. In the preferred form of the present invention, the illumination of the window area 25 is accomplished by providing a window in the handle member to enable the light generated by the optical cable 27 to shine therethrough as the optical cable 27 extends through the interior of the handle member 20. The handle member 20 also preferably includes a flush port 51 to assist in the cleaning and re-sterilization of the handle member.

The handle member 20 may also have an elongated rod 26 that extends upwardly from the first handle member end portion 22. The elongated rod 26 allows the retractor 10 to be fixed or grasped by various operating table mechanisms known in the art so that the retractor 10 may be fixed in a desired position. These known operating table mechanisms are presently used to support various types of equipment around the surgical field and are typically attached at one end to the operating table and include one or more manipulable joints to allow the user to adjust the orientation of the medical device relative to the patient and the operative field. The use of the operating table mechanism and the elongated rod 26 allows the retractor 10 to be maneuvered into the desired position by the physician's assistant and then fixed in the desired relative position thus freeing both of the physician's assistant's hands for the dissection of the exposed vessel while maintaining the skin bridge.

Figure 8A:
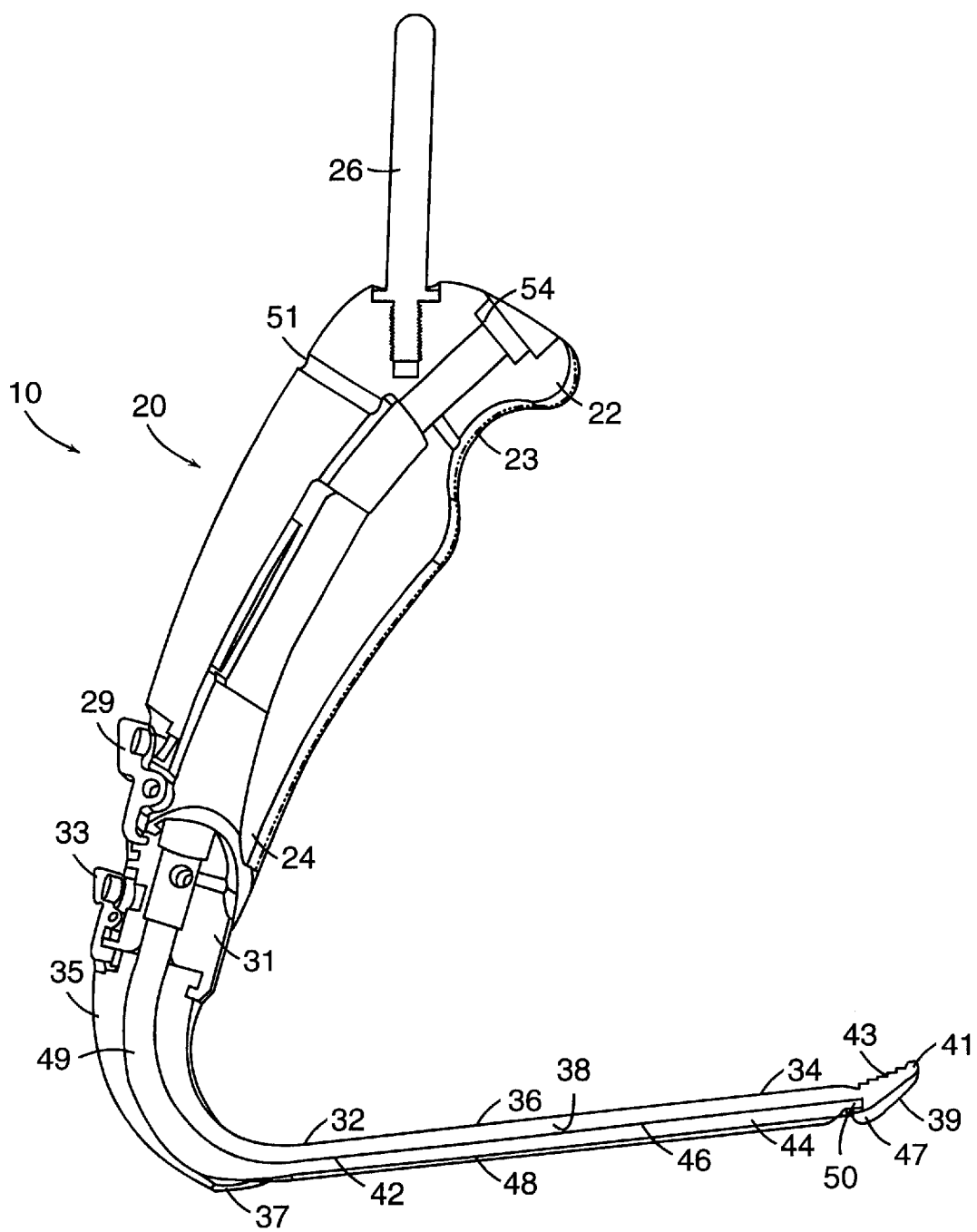
FIGS. 8A and 8B are enlarged side views of an alternate preferred form of an illuminated retractor according to the present invention with a connector at the upper end of the handle member for connecting a standard optical cable to a short optical cable in the handle member.
Figure 8B:
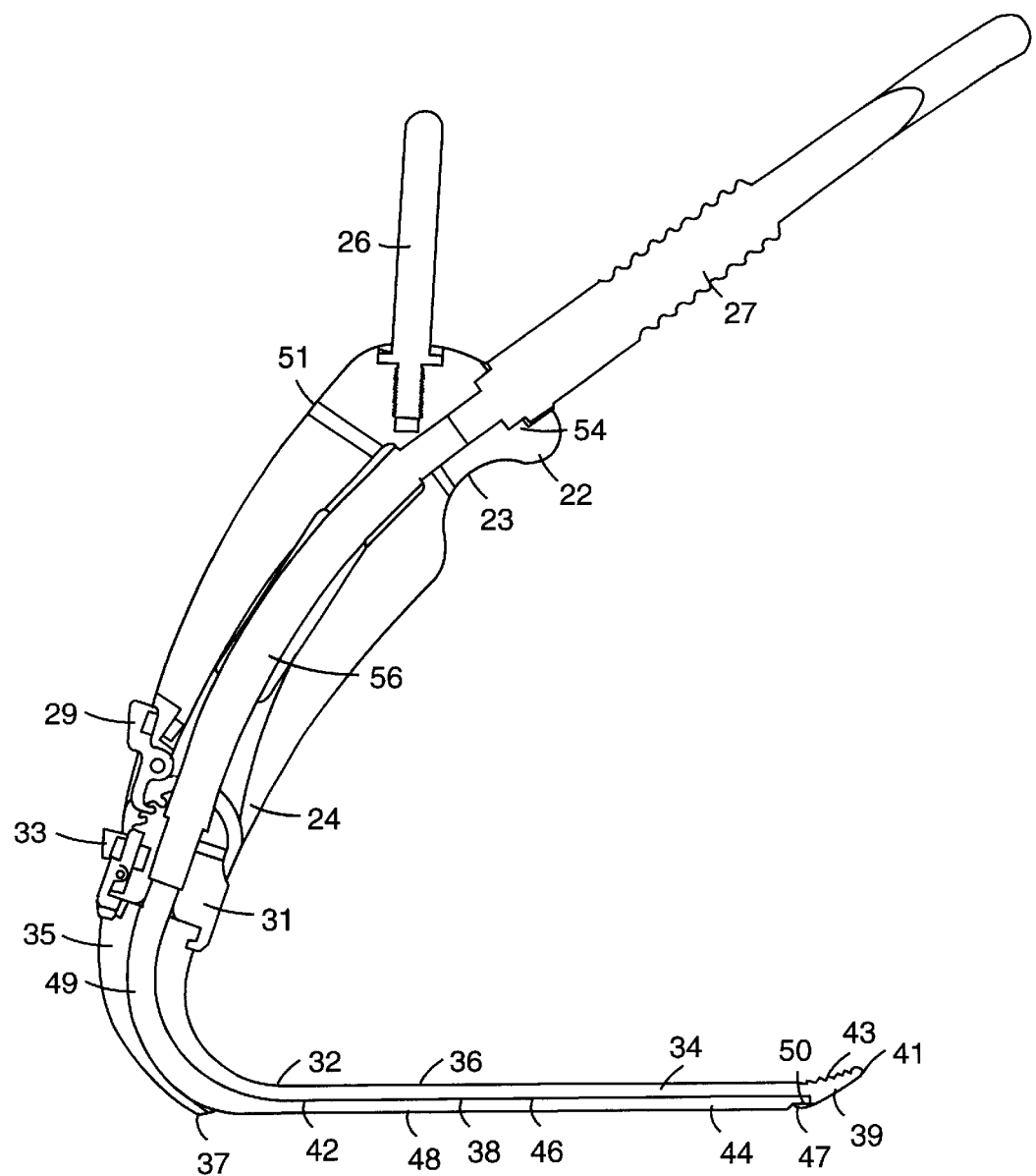

The first handle member end portion 22 of the present invention also preferably includes an optical cable 27 extending therefrom. In the preferred form of the present invention, the optical cable 27 is flexible and extends from the twist connector 31 on the proximal portion of the handle member 20 to a conventional light source (not shown). In an alternate preferred form of the present invention, the first handle member end portion 22 includes a second connector 54 (FIGS. 8A and 8B) thereon to allow the user to connect a standard length of optical cable thereto which is then connected to the conventional light source. In this embodiment, an optical cable 27 is connected to a short cable 56 at the second connector and then the second elongate section is connected to the short cable 56 at the twist connector 31.

The second handle member end portion 24 is preferably pivotally connected to the first elongate section 30. As shown, the second handle member end portion 24 preferably includes a depressible pivot knob 29 thereon which actuates the hinge/pivot mechanism located in the interior of the handle member 20. Depression of the pivot knob 29 enables the user to pivot the first elongate section 30 relative to the handle member 20. When the pivot knob 29 is released, the first elongate section 30 and the handle member 20 are fixedly retained relative to each other. In the preferred form of the present invention, the hinge/pivot mechanism provides a mechanical joint to connect the first elongate section to the handle member while the optical cable 27 or short cable 56 are preferably flexible and provide for the transfer of light energy therethrough. Therefore, the pivoting of the handle member relative to the first elongate section does not affect the connection between the optical cable or short cable and the second elongate section which occurs through the twist connector.

The second handle member end portion 24 also preferably includes a twist connector 31 thereon. In the preferred form of the present invention, the twist connector 31 allows for the releasable connection of the first elongate section 30 and the second elongate section 40 to the handle member 20 in such a manner so as to allow for the transmission of light through the optical cable 27 and into the second elongate section 40 and to provide for the secure attachment between the handle member 20 and the first elongate section 30. As shown in the Figures, the twist connector preferably includes a key and keyway configuration that allows for the secure and quick connection of the first elongate section to the handle member. Additionally, a preferred form of this connection includes the increase in resistance turning of these members and the secure positioning of the shaft shaped portion relative to the end of the optical cable or short cable. The first elongate section 30 and the second elongate section 40 may be quickly removed from the twist connector 31 on the handle member 20 by depressing the connector knob 33 and then rotating the first elongate section and second elongate section at least one-fourth turn relative to the handle member 20 to release the keys form the keyway. The use of the twist connector 31 and the connector knob 33 allow the user to quickly and conveniently attach different first elongate sections and/or different second elongate sections to the handle member 20 as desired. Although the preferred form of the connector between the handle member and the first elongate section is described herein as a twist connector, it is anticipated that a variety of connections, such as bayonet, snap or threaded connections may be used, provided that the optical cable and shaft shaped member of the second elongate section are securely and operatively connected thereby.

The first elongate section 30 of the retractor 10 is preferably made of a rigid metal or similar material having sufficient strength to support the skin bridge during use. The first elongate section preferably has a rectangular or blade shaped configuration with a cross section on the outer surface thereof that is slightly curved to assist in the formation of the skin bridge. The first elongate section also includes a first elongate proximal end portion 34, a first elongate distal end portion 32, a first elongate outer surface 36, a first elongate inner surface 38 and a shaft portion 35. As shown in the drawings, the first elongate outer surface 36 and the first elongate inner surface 38 extend generally linearly from the proximal end portion 34 of the first elongate section 30 to a location near the distal end portion 32 of the first elongate section 30. More specifically, as the first elongate section 30 extends distally beyond the first elongate distal end portion 32, the first elongate section 30 tapers from the generally flat contoured shape into a generally circular and preferably hollow curved shaft portion 35. The shaft portion 35 preferably includes a circular bend to form a generally perpendicular or acute angle with respect to the elongate connector and handle member 20. As shown, the shaft portion 35 is also preferably a cylindrical member having a side slot 37 extending lengthwise therealong. As described more fully below, the side slot 37 is formed to receive a portion of the second elongate section laterally inserted therethrough for the connection of the light source to the second elongate section via the twist connector 31. Additionally, and as described in further detail below, the outer curvature of the shaft portion 35 functions to shield the user from the light emitted from the distal portion of the second elongate section 40 so that the light does not reflect into the user's eyes as the tissue is dissected away from the blood vessel.

The first elongate proximal end portion 34 preferably has a rounded shape or a smoothly radiused pointed shape with a nose cone or shroud shaped member 39 thereon. The shroud member 39 is preferably shaped to allow the retractor 10 to be pushed into the small incision made by the physician's assistant and thrust forward and maneuvered through the connective tissue between the subcutaneous tissue and the vessel to be harvested. As shown, the shroud member 39 includes an upper proximal portion 41 that extends a short distance above and proximally from the lengthwise dimension of the first elongate outer surface 36 and preferably forms a blunt tip surface thereon. As shown, the blunt tip surface is also preferably tapered so as to reduce the insertion force and trauma as the shroud member 39 is inserted into the tissue. The upper proximal surface of the shroud member 39 also preferably includes a plurality of serrations 43 extending laterally across the upper surface thereof.

The shroud member 39 also preferably includes a lower distal portion 45 that extends downwardly and distally from the proximal end portion of the first elongate section. As shown, the lower distal portion 45 of the shroud member 39 preferably forms a recessed area 47 in combination with the first elongate inner surface. The recessed area 47 is shaped to receive and securely retain a portion of the proximal end portion of the second elongate section 40 therein. The width and thickness of the shroud member 39 also preferably increases from the upper proximal portion 41 to the lower distal portion 45 to assist in the tissue dissection procedure.

The second elongate section 40 has a second elongate proximal end portion 44, a second elongate distal end portion 42, a second elongate outer surface 46, a second elongate inner surface 48 and a shaft shaped portion 49. As shown in the drawings, the second elongate outer surface 46 and the second elongate inner surface 48 are preferably generally flat in cross section and extend from the proximal end portion 44 of the second elongate section 40 to near the distal end portion 42 of the second elongate section 40. More specifically, as the second elongate section 40 extends distally beyond the second elongate distal end portion 42, the second elongate section 40 tapers into a shaft shaped member 49 which then curves to match the curvature and inner dimension of the shaft portion 35 of the first elongate section 30 and is receivable through the side slot 37. This bend portion in the shaft shaped member 49 of the second elongate section 40 also allows the transition between the shaft shaped member 49 and the distal end portion 42 of the second elongate section 40 to be surrounded by the distal 32 end portion and shaft portion 35 of the first elongate section 30 to minimize the glare from the shaft shaped member 49 and distal portion of the second elongate section and also to protect the shaft shaped member 49 as it curves and extends to the twist connector 31. Furthermore, the shaft shaped member 49 of the second elongate section 40 is preferably spaced apart from the inner surface of the shaft portion 35 of the first elongate section 30 to reduce the potential for the buildup of heat from the light energy passing through the second elongate section. The second elongate outer surface 46 and the second elongate inner surface 48 correspondingly are eliminated as the second elongate section 40 tapers into the shaft shaped member 49.

The second elongate section 40 is preferably an elongate and rectangular or blade shaped member, although it is anticipated that the second elongate section may also be formed as a single or multiple light fiber member. The second elongate section is also preferably substantially transparent and is made of a transparent plastic, such as a transparent acryl resin, which has the benefit of being highly resistant to breakage while retaining the ability to flex or deform under pressure and then return undamaged to the original, unstressed configuration. However, the second elongate section 40 may also be made of glass or other types of known substantially transparent material in various configurations described herein.

The second elongate outer surface 46 of the second elongate section 40 is configured such that the first and second elongate sections 30, 40 are preferably substantially parallel along the substantial length of the first and second elongate sections 30, 40. The second elongate section 40 may be connected to the first elongate section 30 by inserting the second elongate proximal end portion 44 into the recessed area 47 of the shroud member 39 while the second elongate member distal end portion and shaft shaped member 49 are inserted into the side slot 37 in the shaft portion 35 of the first elongate section 30 to securely retain the second elongate section adjacent to the first elongate section and engage the optical cable 27 with the second elongate section 40 through the twist connector 31. As shown, the second elongate proximal end portion 44 preferably includes a lip member 50 thereon which is sized to be received in the recessed area 47 of the shroud member 39. Additionally, the elongate proximal end portion 44 preferably includes a chamfered surface 52 adjacent to the lip member 50. The chamfered surface 52 is preferably at an angle of between about 30 degrees and 60 degrees and more preferably at an angle of about 45 degrees and functions similar to a headlight to project light from the forward end of the second elongate section and beyond the end of the retractor. Therefore, light is preferably passed outwardly from the second elongate section and forwardly from the chamfered surface to illuminate the tissue in the skin bridge.

Alternately, the second elongate section may be connected to the first elongate section in any manner known in the art that is within the level of ordinary skill of one in the surgical field. For example and less desirably than the embodiment described above, the second elongate outer surface 46 may be chemically bonded to the first elongate inner surface 38 through the use of an adhesive or by other chemical bonding means known to one skilled in the art. This chemical bonding may permanently affix the first and second elongate sections 30, 40 or may preferably allow the first and second elongate sections 30, 40 to be releasably connected for ease of sterilization of the respective elongate sections 30, 40. Alternately, if the second elongate section is a light fiber element, the light fiber element may be threaded through various retention members located along the lengthwise dimension of the first elongate section.

The second elongate proximal end portion 44 of the second elongate section 40 has a rounded shape or, alternatively, a smoothly radiused pointed shape. The shape of the second elongate proximal end portion 44 is sized to be securely received in the recessed area 47 of the shroud member 39 and so that flexing of the shroud member 39 and first elongate section will not separate the second elongate section from the recessed area.

As described briefly above, the first elongate section 30 preferably has a slightly curved cross-sectional shape. The curved cross-section of the first elongate section 30 causes the first elongate outer surface 36 to be convex. The convex cross-sectional shape of the first elongate outer surface 36 of the first elongate section 30 aids in the prevention of unnecessary trauma to the retracted tissue because the first elongate outer surface 36, which is in contact with the subcutaneous tissue when the pulling force is applied to the retractor 10, presents no sharp edges that could cause tearing of the tissue. Rather, the shape aids in distributing the force applied to the retracted tissue by the first elongate section 30. The first elongate inner surface 38 of the first elongate section 30 is preferably generally flat in cross section to further reinforce the first elongate section. Alternately, the first elongate inner surface may be generally concave in crosssection. The second elongate outer surface 46 of the second elongate section 40 may also preferably define a generally flat surface in cross-section that is complementary to the preferred cross-sectional shape of the inner surface 38 of the first elongate section 30. As will be obvious to one skilled in the art, if a complementary fit of the second elongate outer surface 46 of the second elongate section 40 and the inner surface 38 of the first elongate section 30 is desired, the outer surface 46 of the second elongate section 40 may have nearly any geometric cross-section that allows the second elongate outer surface 46 to complementarily fit against the inner surface 38 of the first elongate section 30, as there is no requirement that the first elongate inner surface 38 be concave in cross-section.

There is also no constraint requiring that the outer surface 46 of the second elongate section 40 be complementarily shaped to the inner surface 38 of the first elongate section 30. The only constraint on the shape of the geometric crosssection of the second elongate section 40 is that the chosen geometric crosssection should allow the second elongate section 40 to be protected, by means known in the art, by the first elongate section 30 such that the first and second elongate sections 30, 40 are preferably operatively interconnected and complementary to each other. Even more preferably, the first and second elongate sections are substantially parallel to each other while also providing the optimal and desired illumination for the procedure.

In order to enhance the reflective qualities of the retractor 10, the first elongate inner surface 38 of the first elongate section 30 preferably has a mirrored or reflective surface. Also, the second elongate inner surface 48 of the second elongate section 40 preferably has a machined micro lens surface to refract the light in the desired direction or directions. The mirrored surface of the first elongate inner surface 38 and the surface of the second elongate inner surface 48 act to minimize the loss of the light intensity that is provided to the surgical field by the illuminated retractor 10. Alternatively, the second elongate inner surface may include a reflective coating or graded dot surface thereon to reflect the light generated through the second elongate section outwardly through the second elongate outer surface 46. Additionally, the second elongate section may be formed so as to specifically direct the light forwardly or towards the proximal end of the retractor to direct the illumination forwardly beyond the shroud member 39 thereby assisting the user to illuminate the area of interest. Because the second elongate section of the present invention is readily removable, it is anticipated that a variety of second elongate sections may be used, including second elongate sections that are formed to direct the illumination forwardly and/or to one or both sides of the retractor as desired by the user. As shown, the illumination from the retractor is preferably at an angle of about forty-five degrees forwardly of the retractor, although this forward orientation of the light may be oriented to be between thirty degrees and ninety degrees with respect to the lengthwise dimension of the retractor. Similarly, the second elongate section may be formed to direct light sideways from the retractor at an angle of between about fifteen degrees and ninety degrees and more preferably about 45 degrees with respect to the retractor.

The light energy passes from the light source, through the optical cable 27 and enters the second elongate section at the end portion of the shaft shaped member 49 adjacent to the twist connector 31. In the alternate preferred embodiment shown in FIGS. 8A and 8B, the light energy passes from the light source, through the optical cable 27, to the second connector 54 and into the short cable 56. From the short cable 56, the light energy passes to the twist connector and into the shaft shaped member on the second elongate section. The shaft shaped member 49 of the second elongate section 40 directs the illumination to the second elongate distal end portion 42 of the second elongate section 40 and allows light energy to enter the second elongate section 40. The light energy fills the second elongate section 40, turning the second elongate section 40 into a "light pipe." The light energy is, in turn, radiated from the second elongate section 40, and particularly from the inner surface 48 of the second elongate section 40 between the distal end portion and proximal end portion of the second elongate section and preferably from the chamfered surface 52 on the proximal end portion of the second elongate section. The light is then directed into the subcutaneous space between the vessel and the subcutaneous tissue exposed by the retractor 10. Since substantially the entire length of the second elongate section 40 is illuminated, a large, well illuminated surgical field extends the substantial length of the second elongate section 40 of the retractor 10. This allows the physician's assistant to dissect the vein in a less invasive manner without the need for viewing the surgical field through endoscopic visual devices.

The twist connector 31 couples the optical cable 27 to the shaft shaped member 49 of the second elongate section 40. The twist connector 31 is adapted to receive and releasably retain the shaft portion 35 of the first elongate section and the shaft shaped member 49 of the second elongate section therein to couple the shaft shaped member 49 to the optical cable 27 and to connect the first elongate section to the handle member 20. In this manner, light can be provided from the light source via the optical cable to the shaft shaped member 49 of the second elongate section 40 so that the second elongate section 40 is illuminated.

To aid in the dissection of the connective tissue and to more efficiently use the force applied to the retractor 10 as the retractor is maneuvered through and around the connective tissue, the preferred form of the present invention uses the shroud member 39 that functions as a bent tip having an upper proximal portion 41 which is connected to the proximal end portion 34 of the first elongate section 30. Preferably, the upper proximal portion 41 of the shroud member 39 functions as a simple extension, from the proximal end portion 34 of the first elongate section 30. As shown, the upper proximal portion 41 of the shroud member 39 preferably includes a slightly bent tip longitudinal axis and forms an obtuse angle relative to the longitudinal axis of the first elongate section. This obtuse angle can be between 95°–175° and is preferably about 160°.

Referring further to the drawings, the upper proximal portion 41 of the shroud member 39 preferably has a rounded shape or a smoothly-radiused pointed shape that allows the retractor 10 to be pushed into the small incision made by the physician's assistant and maneuvered through the connective tissue between the subcutaneous tissue and the vessel to be harvested. The upper proximal portion 41 of the shroud member 39 further has an outer surface having a plurality of dissecting serrations 43 thereon. Each of these serrations 43 are preferably oriented at a substantial right angle to the lengthwise dimension of the upper proximal portion 41 of the shroud member 39. It is contemplated that the serrations 43 may be placed at an angle, other than the right angle described above, relative to the upper proximal portion 41 of the shroud member 39. It is also contemplated that the serrations 43 might be placed at a series of angles to form a graphic series of serrations 43 to increase the tissue gripping ability of his portion of the retractor. One example of which would be the use of a plurality of arrow, or v-shaped, serrations 43 with the point of the arrow oriented toward the proximal end portion 34 of the first elongate section 40.

A purpose of the upper proximal portion 41 of the shroud member 39 is to help the physician's assistant translate some of the applied force to the retractor 10 into a dissecting force by letting the upper proximal portion 41 of the shroud member 39, with the dissecting serrations 43, perform some of the required dissecting work. By using the retractor 10 accomplish some of the dissecting required by the vessel harvesting procedure, the physician's assistant can, while still performing the procedure in a less invasive manner, more rapidly complete the surgical procedure, which results in reduced surgical time and reduces the possibility of trauma to the patient from the surgery.

The present invention has been described in reference to use in harvesting blood vessels. It would be obvious to one skilled in the art that the present invention could also be used in other minimally invasive surgical procedures in which the illumination of the minimally invasive surgical field is desired. Furthermore, although the present invention has been described with reference to specific details of the preferred embodiments thereof, it is not intend that such detail should be regarded as limitations upon the scope of the invention except as and to the extent that they are included in the accompanying claims.

What is claimed is:

1. An illuminated surgical retractor comprising:

handle member having a first handle member end portion and a second handle member end portion;

a first elongate section having a first elongate proximal end portion, a first elongate distal end portion, and a first elongate inner surface extending from the first elongate proximal end portion to near the first elongate distal end portion, the second handle member end portion of said handle member pivotally connected to the first elongate distal end portion of said first elongate section such that said handle member forms an adjustable acute angle with said first elongate section;

a second elongate section having a second elongate proximal end portion, a second elongate distal end portion, and a second elongate outer surface extending from the second elongate proximal end portion to near the second elongate distal end portion, and a second elongate inner surface extending from the second elongate proximal end portion to near the second elongate distal end portion, said second elongate section connected to said first elongate section such that said first and second elongate sections are substantially parallel; and said second handle member end portion having a pivotal connector associated therewith and said pivotal connector pivotally couples the first elongate section and the handle member and said second handle member end portion is adapted to optically couple the second elongate section to a source of illumination so that said second elongate section is substantially illuminated.

2. The illuminated surgical retractor of claim 1, wherein said first elongate section has a first elongate outer surface that defines a generally convex curve in cross-section, and wherein the first elongate inner surface of said first elongate section defines a generally flat shape in cross-section.

3. The illuminated surgical retractor of claim 1, wherein the second elongate outer surface of said second elongate section defines a generally flat surface in cross-section.

4. An illuminated surgical retractor comprising:

a handle member having a first handle member end portion and a second handle member end portion;

a first elongate section having a lengthwise dimension and a first elongate proximal end portion, a first elongate distal end portion, and a first elongate inner surface extending from the first elongate proximal end portion to near the first elongate distal end portion, the second handle member end portion of said handle member operatively connected to the first elongate distal end portion of said first elongate section such that said handle member forms an acute angle with said first elongate section;

a second elongate section having a lengthwise dimension and a second elongate proximal end portion, a second elongate distal end portion and a second elongate outer surface extending from the second elongate proximal end portion to near the second elongate distal end portion, and a second elongate inner surface extending from the second elongate proximal end portion to near the second elongate distal end portion, said second elongate section being generally aligned with the lengthwise dimension of the first elongate section such that said first and second elongate sections are substantially parallel, said second elongate section defining an illumination output portion; and said second handle member end portion having a pivotal connector associated therewith and said pivotal connector pivotally couples the first elongate section and the handle member and said second handle member end portion is adapted to optically couple the second elongate section to a source of illumination so that said second elongate section is illuminated.

5. The illuminated surgical retractor of claim 4, wherein the first elongate section has a shaft portion thereon between the distal end portion and the pivotal connector.

6. The illuminated surgical retractor of claim 5, wherein said shaft portion substantially surrounds at least a portion of said second elongate section.

7. The illuminated surgical retractor of claim 4, wherein at least a portion of said second elongate section is surrounded by at least a portion of said first elongate section.

8. The illuminated surgical retractor of claim 4, wherein the first elongate section includes a shroud member thereon and said shroud member includes a recessed area thereon to receive at least a portion of said second elongate section therein.

9. An illuminated surgical retractor for use in a patient comprising:

a handle member having a first handle member end portion and a second handle member end portion;

a first elongate section having a first elongate proximal end portion, a first elongate distal end portion, and a first elongate inner surface extending from the first elongate proximal end portion to near the first elongate distal end portion, the second handle member end portion of said handle member connected to said first elongate section such that said handle member forms an acute angle with said first elongate section;

a second elongate section having a second elongate proximal end portion, a second elongate distal end portion and a second elongate outer surface extending from the second elongate proximal end portion to near the second elongate distal end portion, and a second elongate inner surface extending from the second elongate proximal end portion to near the second elongate distal end portion, said second elongate section connected to said first elongate section such that said first and second elongate sections are substantially aligned, the second elongate distal end portion of said second elongate section defining an illumination output member; and a shroud member on the proximal end portion of the first elongate section wherein the shroud member includes an upwardly extending portion and a downwardly extending portion and a recessed area therein for the receipt of at least a portion of the second elongate section therein.

10. The illuminated surgical retractor of claim 9, wherein said handle member has an elongated rod extending from the handle member and wherein elongate rod is sized to be engaged by an operating table mechanism to retain the retractor in a desired position relative to the patient.

11. The illuminated surgical retractor of claim 9, wherein said handle member is operatively connected to said first elongate section by a pivotal connector.

12. The illuminated surgical retractor of claim 11, wherein said first elongate section is movable at an acute angle relative to the handle member.

13. The illuminated surgical retractor of claim 11, wherein said handle member further includes a socket member for releasably receiving the first elongate section therein and optically coupling the second elongate section to a source of illumination.

14. The illuminated surgical retractor of claim 11, wherein said pivotal connector enables said second elongate section to be interchangeable with respect to the first elongate section.

15. The illuminated surgical retractor of claim 9, wherein said shroud member is oriented at an obtuse angle with respect to said first elongate section.

16. The illuminated surgical retractor of claim 15, wherein said shroud member includes serrations thereon.

17. The illuminated surgical retractor of claim 9, wherein at least a portion of said second elongate section is surrounded by at least a portion of said first elongate section.

18. The illuminated surgical retractor of claim 9, wherein said at least a portion of said handle member is illuminated.

19. The illuminated surgical retractor of claim 9, wherein at least a portion of said first elongate section substantially surrounds at least a portion of said second elongate section and said at least a portion of said second elongate section is removable therethrough.

20. The illuminated surgical retractor of claim 9, wherein said second elongate section is laterally insertable into engagement with said first elongate section.

21. The illuminated surgical retractor of claim 9, wherein said first elongate section is rotatable with respect to said handle member for removal therefrom.

22. An illuminated surgical retractor comprising:
- a handle member having a first handle member end portion and a second handle member end portion and at least a portion thereof that is illuminated in use;
- a first elongate section having a first elongate proximal end portion, a first elongate distal end portion, and a first elongate inner surface extending from the first elongate proximal end portion to near the first elongate distal end portion, the second handle member end portion of said handle member connected to the first elongate distal end portion of said first elongate section such that said handle member is pivotal with respect thereto and forms an acute angle with said first elongate section;
- a second elongate section having a second elongate proximal end portion, a second elongate distal end portion, and a second elongate outer surface extending from the second elongate proximal end portion to near the second elongate distal end portion, and a second elongate inner surface extending from the second elongate proximal end portion to near the second elongate distal end portion, the second elongate distal end portion of said second elongate section defining an illumination output member.

23. The illuminated surgical retractor of claim 22, wherein the second longate section is substantially illuminated.

24. The illuminated surgical retractor of claim 22, wherein said second longate section includes a shaft shaped portion that is substantially enclosed by at least a portion of said first elongate section.

25. The illuminated surgical retractor of claim 22, wherein said first elongate section is pivotal with respect to said handle member.

26. The illuminated surgical retractor of claim 22, wherein the acute angle formed between said handle member and said first elongate section is pivotal from about 30° to 95°.

27. An illuminated surgical retractor comprising:
- handle member having a first handle member end portion and a second handle member end portion;
- a first elongate section having a first elongate proximal end portion and a first elongate distal end portion with a first elongate inner surface extending between the first elongate proximal end portion and the first elongate distal end portion and said second handle member end portion of said handle member is connected to said first elongate section;
- a second elongate section having a second elongate proximal end portion and a second elongate distal end portion with a second elongate outer surface extending between the second elongate proximal end portion and the second elongate distal end portion, a second elongate inner surface extending between the second elongate proximal end portion and the second elongate distal end portion, the second elongate distal end portion of said second elongate section defining an illumination input end portion;
- a connector releasably coupling the illumination input end portion to an optical cable; and
- a pivotal connector pivotally coupling the handle member to the first elongate section.

28. The illuminated surgical retractor of claim 27, wherein said second elongate section is oriented at an acute angle with respect to said handle member.

29. The illuminated surgical retractor of claim 27, wherein at least a portion of said second elongate section is surrounded by at least a portion of said first elongate section.

30. The illuminated surgical retractor of claim 27, wherein said first elongate section includes a shroud member thereon and said shroud member releasably connects said second elongate section to said first elongate section.

31. The illuminated surgical retractor of claim 27, wherein at least a portion of said first elongate section substantially surrounds a shaft portion on said second elongate section.

32. The illuminated surgical retractor of claim 27, wherein said second elongate section forms a light pipe and includes a surface thereon for directing light forwardly therefrom.

33. The illuminated surgical retractor of claim 27, wherein at least a portion of said handle member and said second elongate section are illuminated in use.

34. An illuminated surgical retractor for illuminating the subcutaneous space between a vessel and the subcutaneous tissue of a patient, the retractor comprising:
- a handle member having a first handle member end portion and a second handle member end portion with a gripping area therebetween for gripping by the user and an optical cable extending therethrough;
- an elongate first elongate section sized to be positioned in the subcutaneous space between a vessel and subcutaneous tissue and having a first elongate proximal end portion and a first elongate distal end portion with a first elongate inner surface extending between the first elongate proximal end portion and the first elongate distal end portion, the second handle member end portion of said handle member connected to the first elongate section;
- an elongate second elongate section having a second elongate proximal end portion and a second elongate distal end portion with a second elongate outer surface extending generally parallel to said first elongate section and between the second elongate proximal end portion and the second elongate distal end portion and a second elongate inner surface extending between the second elongate proximal end portion and the second elongate distal end portion, the second elongate section further including an illumination input end portion thereon and at least a portion of said illumination input end portion is substantially surrounded by a portion of said first elongate section;
- a connector optically coupling the illumination input end portion to the optical cable;
- a pivotal connector for pivotally connecting the handle member and the first elongate section such that the first elongate section is movable at an acute angle relative the handle member; and
- wherein at least a portion of said second elongate section is laterally removable from said first elongate section.

35. The illuminated surgical retractor of claim 34, wherein said proximal end portion of said second elongate section is releasable from a shroud member on the proximal end portion of the first elongate section.

36. The illuminated surgical retractor of claim 34, wherein said second elongate section is formed to direct light laterally therefrom and beyond the first elongate section.

* * * * *

UNITED STATES PATENT AND TRADEMARK OFFICE
CERTIFICATE OF CORRECTION

PATENT NO. : 6,322,499 B1
DATED : November 27, 2001
INVENTOR(S) : Douglas Gerald Evans and Donna Dimarco Holland It is certified that error appears in the above-identified patent and that said Letters Patent is hereby corrected as shown below:

Column 1,
Line 13, replace "and boffi applications" with -- and both applications --;

Column 2,
Line 31, replace "uincisions" with -- incisions --;

Column 6,
Line 10, replace "relative to the second is elongate section" with -- relative to the second elongate section --;
Line 18, replace "onequarter turn" with -- one-quarter turn --;

Column 8,
Line 35, replace "manipulable" with -- manipulatable --;

Column 14,
Line 46, replace "handle member having" with -- a handle member having --;

Column 17,
Lines 26 and 28, replace "second longate" with -- second elongate --
Line 38, replace "handle member having" with -- a handle member having --.

Signed and Sealed this

Twenty-first Day of May, 2002

*Attest:*

*Attesting Officer*

JAMES E. ROGAN
*Director of the United States Patent and Trademark Office*